United States Patent [19]

Joishy

[11] Patent Number: 5,012,818
[45] Date of Patent: May 7, 1991

[54] TWO IN ONE BONE MARROW SURGICAL NEEDLE

[76] Inventor: Suresh K. Joishy, P.O. Box 641, Abha, Saudi Arabia

[21] Appl. No.: 347,239

[22] Filed: May 4, 1989

[51] Int. Cl.⁵ .............................................. A61B 10/00
[52] U.S. Cl. ...................................... 128/754; 604/44
[58] Field of Search ...................... 128/749, 751, 754; 606/167, 170; 604/44, 51, 115, 164, 167, 170, 173, 188, 239, 264, 272

[56] References Cited

U.S. PATENT DOCUMENTS

| | | | |
|---|---|---|---|
| 3,993,079 | 11/1976 | Gatztanondo | 604/272 |
| 4,099,528 | 7/1978 | Sorenson et al. | 604/44 |
| 4,262,676 | 4/1981 | Jamshidi | 128/754 |
| 4,266,555 | 5/1981 | Jamshidi | 128/754 |
| 4,531,935 | 7/1985 | Berryessa | 604/44 |
| 4,808,157 | 2/1989 | Coombs | 604/44 |
| 4,840,184 | 1/1989 | Garg | 128/754 |
| 4,850,373 | 7/1989 | Zatloukal et al. | 128/754 |

FOREIGN PATENT DOCUMENTS 1424802  9/1988  U.S.S.R. ........................... 128/749

*Primary Examiner*—Max Hindenburg
*Attorney, Agent, or Firm*—Woodard, Emhardt, Naughton, Moriarity & McNett

[57] ABSTRACT

A novel biopsy needle like surgical instrument to obtain both solid bone marrow biopsy and liquid bone marrow aspirate by a new method of obtaining both specimens in a single procedure are disclosed. The needle consists of two heads at the proximal end, two lumina inside its elongated body and two distal openings. Each head contains portal for entry for respective stylets for biopsy and aspiration. The distal end of the needle contains two openings leading to the lumina inside the needle meant for biopsy and aspiration respectively. The proximal one third of the needle is encased in a specially designed handle with grips for the index finger, the thumb and a cap for the hollow of the operators hand.

Upon insertion of the needle in the cortical bone of the iliac crest of the patient the biopsy stylet is withdrawn. Further pushing the needle results in entry of the marrow cavity facilitating entry of a solid core of marrow in the hollow biopsy portion of needle lumen. Without disturbing the needle, the aspiration stylet is withdrawn. Fixing a luer neck syringe to the portal of the aspiration head, liquid marrow can be aspirated with negative pressure from the aspiration lumen. The procedure is completed on withdrawing the needle and expressing the solid core of marrow biopsy using the biopsy probe. Thus, a solid core of marrow specimen and liquid sample of marrow aspirate are obtained with a single entry into the bone.

14 Claims, 8 Drawing Sheets

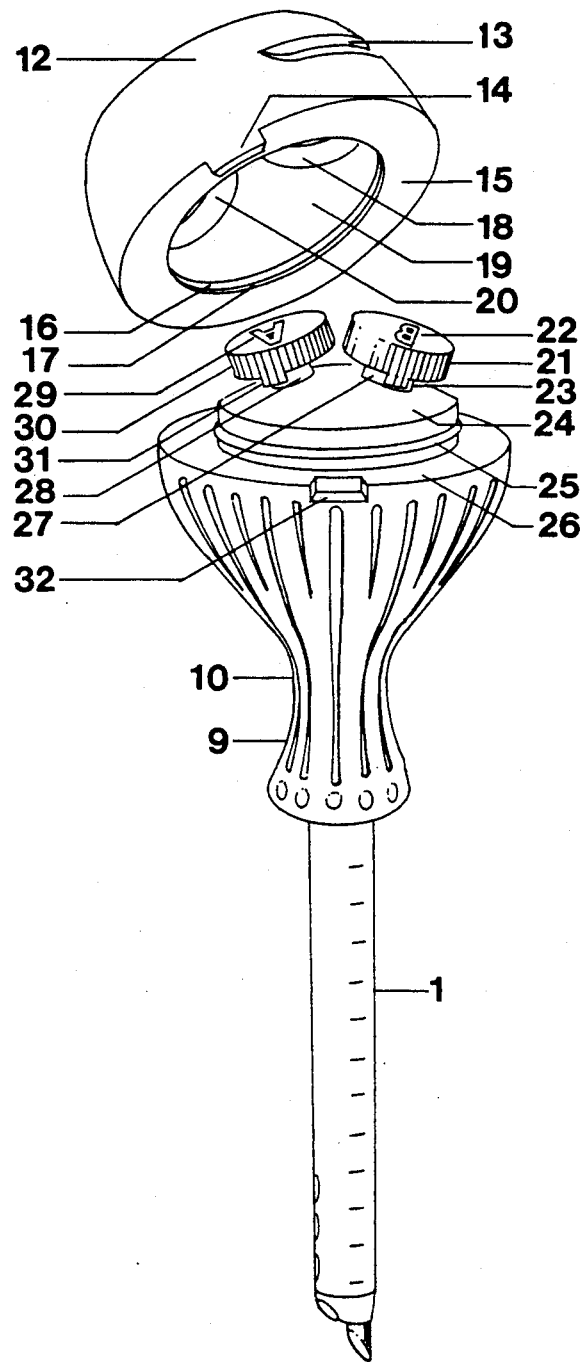
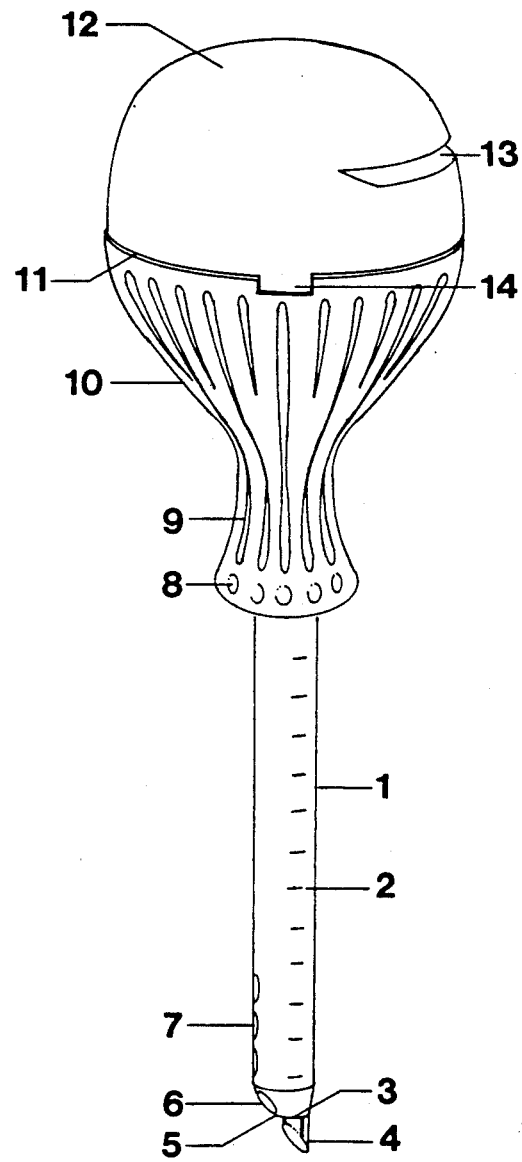
Fig. 1
Fig. 2

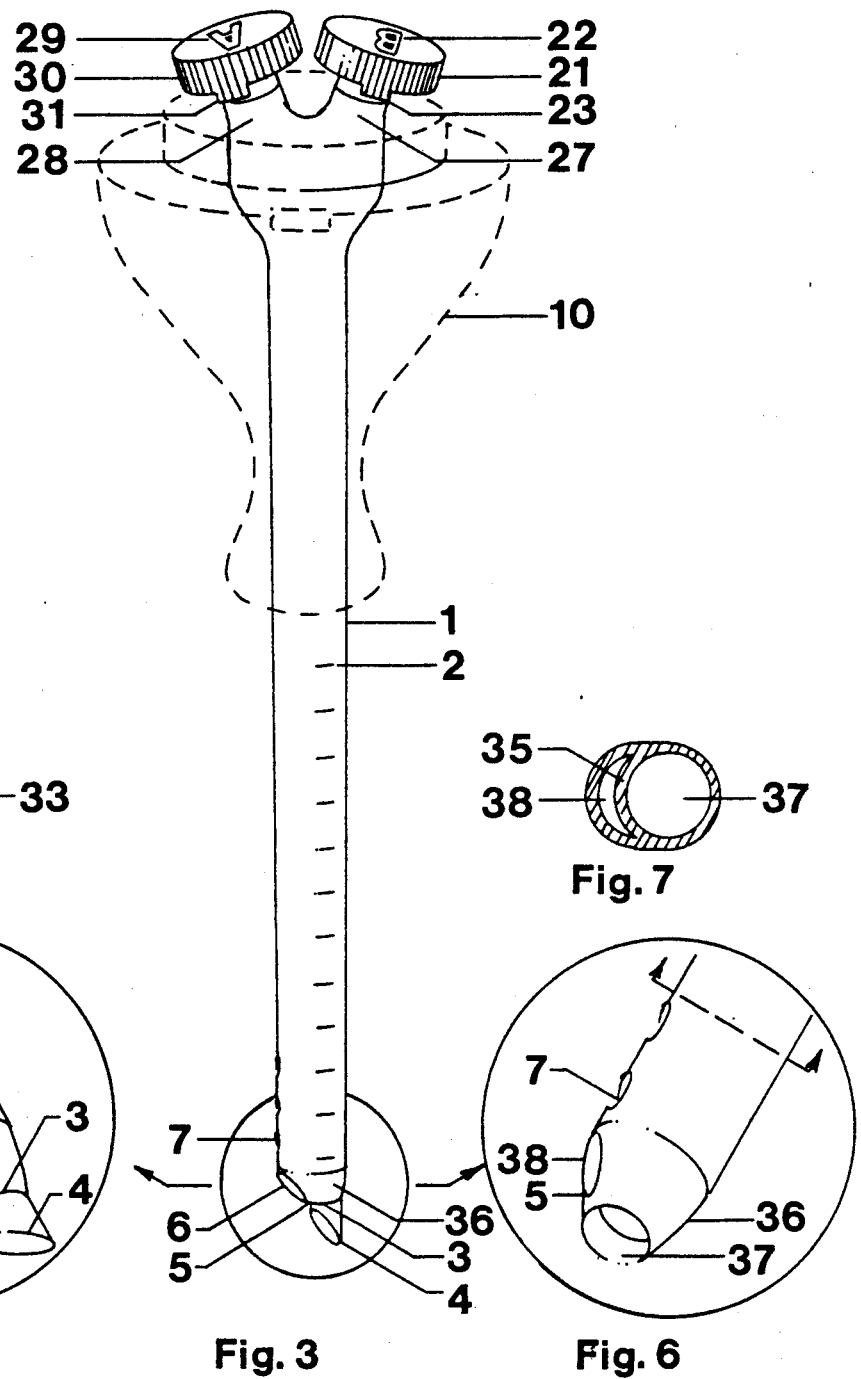

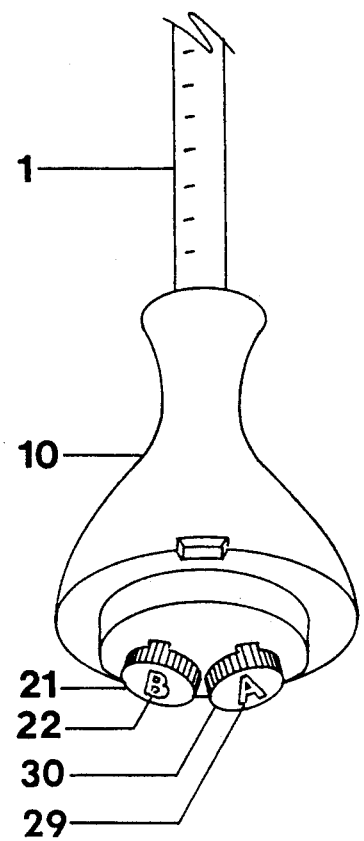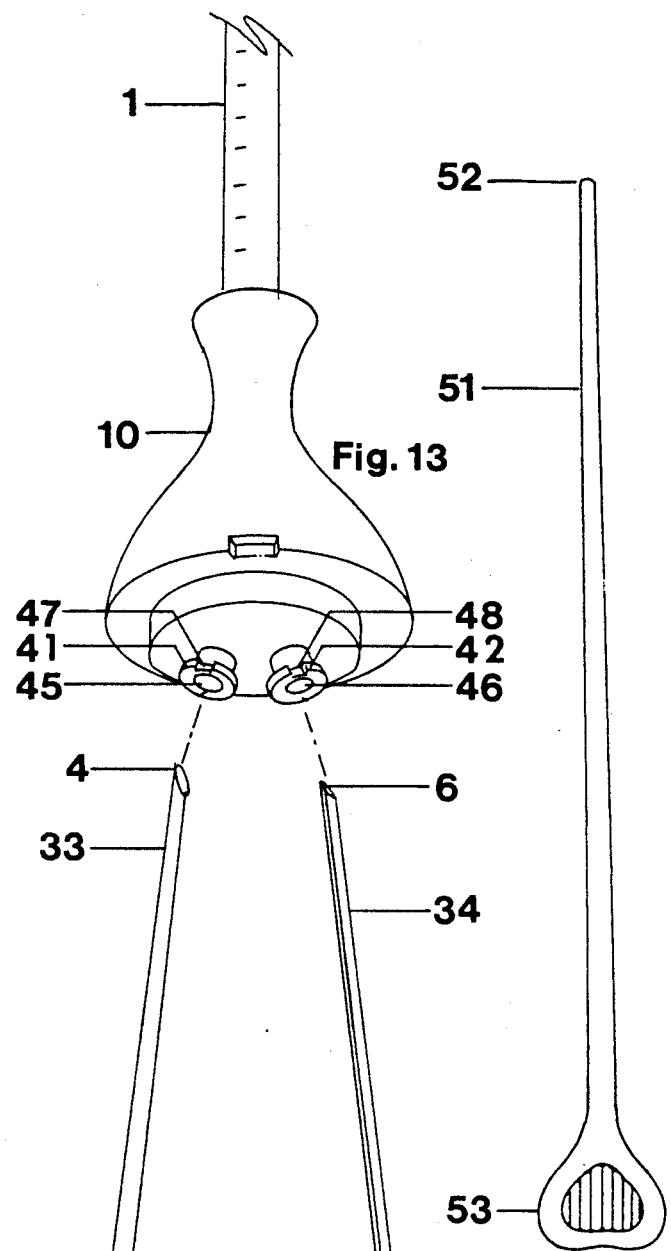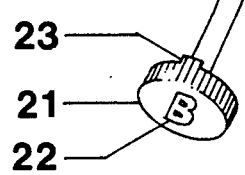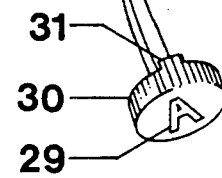

Step A1

Step A2

Step B

Step C1

Step C2

Step D1

Step D2

Step D3

TWO IN ONE BONE MARROW SURGICAL NEEDLE

FIELD OF INVENTION

The present invention relates to surgical biopsy needle like instrument generally used to penetrate the bone and specifically used to obtain bone marrow from iliac crest of hip bone of a patient and a new method of obtaining both specimens of solid marrow core biopsy and fluid marrow aspirate in a single procedure to diagnose diseases of bone marrow and cancers.

BACKGROUND OF INVENTION

Human bone consists of hard outer cortex and a soft medullary cavity containing bone marrow. Marrow consists of stroma or the supporting tissues and its spaces packed by blood cells. Blood cells are manufactures in the bone marrow and are released in the peripheral blood. Therefore it is logical to look at a specimen of marrow to diagnose diseases of blood cells such as leukemias. Traditionally, marrow was obtained by aspiration method using a large bore needle like device and a syringe. Entering the marrow cavity with the needle and aspirating with the syringe causes negative pressure sufficient to break delicate marrow stroma and release of fluid marrow to be aspirated in the syringe. However, this aspiration sample was not sufficient to diagnose some non-blood cell diseases affecting the marrow. For example, marrow forms a very convenient nidus for cancer cells coming from other organs. Aspiration procedure was not sufficent to disloge these cells from the stroma of the marrow. Hence, to diagnose cancers in the bone marrow such as lymphomas and other metastatic cancers it was necessary to obtain intact marrow in solid form. The procedure to obtain a solid sample of marrow is called marrows biopsy. Traditionally, a solid core of marrow biopsy was obtained by pushing a larger bore needle with hollow lumen into marrow cavity. As the needle is pushed, a core of marrow enters the lumen. The needle containing the marrow is withdrawn and the core expressed out using a blunt probe. Current art includes designs that one can aspirate or biopsy the marrow using the same needle but it still requires two separate procedures requiring to penetrate the bone marrow twice albeit close to each other. This means two painful procedures for the patient and sometimes more frequently, depending on the success of the procedure each time.

It should be realised one cannot perform aspiration or biopsy from any bone of the body. A traditional method of obtaining a fluid aspirate of marrow was from the sternum which is a chest bone in the front. The needle used for this purpose is short because sternum is a flat and thin bone and longer needles may penetrate the bone completely and injure vital structures underneath. One should never attempt a biopsy from the sternum even with a shorter needle. There have been inventions disclosed for biopsy of sternum before but those experienced in the field will know not to biopsy the sternum.

Obtaining aspiration and biopsy specimens from a large hip bone is the most popular method due to its safety. However, obtaining marrow specimen from the hip bone, the iliac crest, needs much larger and stronger needle. Considerable force is needed to pierce the bone. To overcome these difficulties, needles have been designed with improved cutting edges and various types of handle to give the operator grip to exert force. Needles with various shapes at their tip are available to get the biopsy without distortion and retaining it within the lumen of the needle while withdrawing. All the available needles however have not overcome the need to reduce the number of procedures less than two to obtain both biopsy and aspiration.

A successful biopsy requires, first, the force with which the needle can penetrate the thick and hard bony cortex. Second, the grip with which the operator can hold the needle in position. Third, the forward force with which the needle can be pushed in the bone. Existing needles do not fulfill these requirements and improvements are still being sought after and still being proposed.

DESCRIPTION OF PRIOR ART

Needle devices of various designs have been in use to aspirate fluid marrow specimen. They all have in common a hollow elongated needle filled with a stylet with sharp tip to penetrate the bone. Upon entering the marrow cavity the stylet is withdrawn and using a syringe at the proximal end of the needle, marrow is aspirated under negative pressure. A popular way of obtaining a solid marrow biopsy specimen is using a larger bore elongated needle with a stylet. After penetrating the bone cortex with the needle the stylet is withdrawn. The needle now remaining hollow is pushed further in the marrow causing a core of marrow to enter the needle. The needle is withdrawn as such and the core inside is pushed out with a blunt probe through the needle lumen. If one desires to obtain fluid marrow specimen, same needle can be used in the manner of aspiration described before. Simple as it may sound, the biopsy procedure is wrought with problems. The hip bone or the iliac crest from which the biopsy is sought has a thick hard bony cortex to penetrate. From the operator point of view, the procedure requires considerable dextrity and force to penetrate the bone. The main problem in this step has been to get a comfortable grip on the needle to exert a forward and twisting motion to penetrate the bone with force. One should remember it is mandatory to use sterile rubber gloves over the hands for the entire procedure. Gloves are great impediment when fingers and hands need to exert force and grip at the same time. Most needles in use have no grips for the fingers except the smooth rounded needle which slips easily. Most needles in use have no grip for the hollow of the palm to exert forward force. As a matter of fact, some needles have stylet heads with sharp edges that causes considerable discomfort and pain to the palms of the operator. In an effort to overcome the shortcomings and improve features for the efficiency of the biopsy needle and operator's comfort the following list of patents disclosed design features which have been conceived:

| U.S. PAT. NO. | PATENTEE | DATE ISSUED |
| --- | --- | --- |
| 1. 3,587,560 | Jacob A Glassman | June 28, 1971 |
| 2. 3,893,445 | Paul W Hofsess | July 8, 1975 |
| 3. 4,266,555 | Khosrow Jamshidi | May 12, 1981 |
| 4. 4,403,617 | Carl W Tretinyak | Sep. 13, 1983 |
| 5. 4,469,109 | Donald N Mehle | Sep. 4, 1984 |
| 6. 4,487,209 | Donald N Mehle | Dec. 11, 1984 |
| 7. 4,543,966 | Abdul M. A. Islam & David R Beven | Oct. 1, 1985 |
| 8. 4,630,616 | Carl W Tretinyak | Dec. 23, 1986 |
| 9. 4,655,226 | Peter F Lee | Apr. 7, 1987 |

It was conceived by Glassman in 1971 that one can obtain a marrow biopsy and a circular ring of cancellous bone using an assembly of inner sharp edged needle and a saw tooth edged outer needle telescoping over inner needle as disclosed in their U.S. Pat. No. 3,587,560. Their concept obtaining a solid marrow by aspiration of a syringe is erroneous. One can obtain only fluid marrow by aspiration. Their diagram showing outer needle can hardly obtain a circular bony cortex. One cannot get a rim of bone because under pressure the cortex is crushed. Neither did they describe which bone they were using to obtain specimen. This procedure has not been in use.

Hofsess in 1975 disclosed a bone marrow biopsy needle designed to obtain biopsy from the sternum. It should be emphasized that sternum should never be used to obtain a biopsy due to the fact it is a very thin and flat bone. One can use it for aspirations only. In his U.S. Pat. No. 3,893,445, he also described a telescoping needle. With the type of handle he described with sharp edges it is hard to exert force on the bone. The needle most popular in use today is described by Jamshidi in the imroved designs disclosed in U.S. Pat. No. 4,266,555. His design of needle tip having smaller diameter than the body of the needle helps to retain biopsy specimens inside the needle. This feature has been adopten in one form or other by other inventors. He improved the stylet head with rounded off plastic mould so it will not hurt the palm while pushing. He also provided a finger grip. The main disadvantages of this popular design is too many parts to be assembled and dismantled. The mould meant for finger grip is too small and slippery and the operator ends up using the bare needle surface for grip. Even though rounded off, the stylet head still hurts the palm because it is small. Though the same needle can be used for obtaining fluid marrow aspirate and a solid core of marrow biopsy, it still needs two separate procedures which means inflicting pain to the patient twice.

Considering the problems with lack of handles on the needle Tretinyak disclosed in U.S. Pat. No. 4,403,617 in 1983, a large flat handle. In another U.S. Pat. No. 4,630,616 he improved upon this handle by another attachment on the stylet head. However, this flat handle is inconvenient for the push required for penetration of hard bone and not in popular use.

Mehle in U.S. Pat. No. 4,469,109 in 1984 described an assembly of marrow aspiration needle with a stylet head that needs twisting to fix in orientation. In another U.S. Pat. No. 4,487,209, he described a biopsy needle similar to the one described by Jamshidi except providing wing devices on the handle of the needle. Again the wings were of no use for either finger grip or palm grip.

Islam and Beven in their U.S. Pat. No. 4,543,966 described a biopsy needle with winged handle similar to the ones described by Jamshidi but made up of metal, some improvements in the styulet tip and needle tip on the same principles described before. This needle offers no advantages to the operators comfort despite its efficiency in obtaining a biopsy specimen.

Lee in U.S. Pat. No. 4,655,226 disclosed handle wings flat and made entirely of metal. Still they cannot be considered comfortable to the operator. Thus there exists a great need for improvement in design to achieve operators comfort and importantly patient comfort. It is to this extent that the presenting invention is directed.

OBJECTIVES OF THE INVENTION

The main object of the invention is to provide a novel needle designed to obtain both biopsy of solid marrow and the sample of fluid marrow specimens. It is further the objective of the invention to describe a novel method of obtaining both solid biopsy and fluid marrow specimens in one procedure minimizing discomfort to the patient.

Another objective of the invention is to minimise discomfort to the operator performing the procedure by designing the invention based upon ergonomic principles. It is an additional objective of the feature of invention to provide a novel method of encasing the needle in a specially designed handle for easy finger grip, thumb grip and palmar grip.

Still a further objective of the invention is to design the instrument requiring no assembly or dismantling of parts to perform the procedure. Obviously, it is the objective of the device to add convenience, increase efficiency and safety, keeping patient comfort in mind. The overall objective of the device is to obtain both marrow aspiratin and biopsy at the same time with high yield and success rate.

SUMMARY OF THE INVENTION

This invention is a surgical intrument for obtaining samples of both marrow aspiration and biopsy comprising of an elongated stainless steel needle with two heads at the proximal end with portals entering into two hollow lumina leading to two openings at the distal end. One of the lumina is large and circular and the other is small and semilunar in shape, both lumina fitting within the circular lumen of the entire needle. The large lumen serves to obtain the solid marrow biopsy and the smaller lumen serves to obtain liquid marrow aspirate. The distal tip of the large lumen is tapered slightly to reduce the diameter of the opening so that while withdrawing the needle from the marrow, the solid biopsy core will stay inside. The distal end of the needle at the aspiration side is provided with fenestrated openings to facilitate aspiration of marrow not only from the main opening at the tip but also from the sides for better yield.

The proximal end of the needle bifurcates leading to two heads each containing a portal of entry. The portals serve two purposes. One, they help to hold the stylet in place while introducing the needle in the marrow cavity by way of a slot in the luer edge. Second, they help to fit a syringe with luer to fit in place while aspirating the marrow. There are two stainless steel stylets. The stylet for the biopsy portion of the needle has circular cross section. Its tip protrudes slightly outside the tip of the lumen with a sharp bone cutting edge. The head of this stylet fits snugly with a lug into the slot of luer edge of the biopsy portal. The stylet for aspiration portion of the needle is semilunar in cross section to fit in the corresponding shape of the lumen. Its tip does not protrude outside the tip of the lumen but stays flush with the cutting surface of the biopsy stylet helping to pierce the bone. The head of aspiration stylet is identical to that of biopsy stylet.

The proximal one thid of the entire needle is encased in a specially designed handle mould made up of synthetic plastic or like material. The handle has two parts. The lower part is the body encasing the needle heads, exposing the portals for aspiration and biopsy. The body portion of the handle is ergonomically designed with curves and grooves to serve as gripping portions for thumb and fingers of operator's hand. The upper portion of the handle is a detachable cap. It fits in snugly over the head of the handle requiring only a gentle push. The cap has a slot for thumb nail to detach it with a gentle pull. The cap has a lug that fits snugly in a shelf like slot in the head of the handle for alignment of cap as well as stability of the cap during operation of the handle, so that it will not slip.

The entire needle has markings outside its surface graduated one centrimeter apart to give an idea to the operator as to the depth of penetration of the needle into the bone.

There is one part only which is not the integral part of the needle. It is an elongated stainless steel biopsy pushing probe. The body of the probe has circular cross section with a diameter slightly less than the biopsy lumen so that it can traverse in it easily to express marrow specimen outside the needle after the procedure. The probe has a flat spatula like handle with linear grooves for easy holding between fingers. The distal tip of the probe has rounded edges so that the biopsy specimen will not be damaged while expressing it outside the needle.

In use, to carry out the procedure, the patent is positioned comfortably on an examination table or bed in a left or right lateral position depending to the side of the iliac crest chosen for marrow biopsy and aspiration. The area of the skin for the needle entry is sterilized with antiseptic solutions and draped with sterile towels after the operator had don sterile gloves. Local anaesthetic is used to anaesthetize the skin, subcutaneous tissue all the way up to the periosteum of the iliac crest preferably at the posterior superior iliac spine.

The entire needle device is picked up from a sterile container. It is to be noted that the needle with handle, the stylets and cap all come assembled and there is no need for the operator to assemble any parts. However, it is always best to check the parts in simple steps. Using the thumb nail grove snap and cap out and check if stylets are in place and they traverse easily. The cap is replaced with a snap with its lug snugly fitting into the slot of the head of the handle.

In a few easy steps the entire procedure of obtaining both solid marrow biopsy and liquid marrow sample can be accomplished in less than one to two minutes! Using a sharp lancet the skin is punctured up to the surface of the periosteum. The head of the needle with its cap on, is gripped in such a way that the thumb and index finger hold the corresponding grooves of the handle. The head with cap fits snugly into the hollow of the palm. It is as easy as holding a screw driver. The needle is introduced into the previously made puncture of the skin and pushed to the periosteum of the iliac crest. Further pushing will fix the cutting biopsy stylet into the cortex of the bone. At this stage the cap is opened, the biopsy stylet is withdrawn and set aside. The cap is snap closed, and the needle is pushed further into the marrow cavity with forward pressure on the handle and twisting of the needle. Looking at the graduated markings on the needle from time to time the cortex is penetrated and distance travelled forward is calculated, which gives the estimate of the length of solid core of marrow that entered the hollow lumen of the biopsy portion of the needle. One can stop pushing forward when 1-2 cm of marrow has entered the needle.

Next step is to obtian liquid marrow sample. The cap is opened and set aside. The aspiration stylet is removed and set aside. A luer neck of a syringe is fit into the aspiration portal. A firm suction is applied by withdrawing the plunger of the syringe. This results in breaking of marrow stroma and release of fluid marrow which is easily aspirated through the distal opening as well as openings at the lateral side of aspiration portion of the needle. When adequate liquid marrow to Technician for making microscopic slides of the marrow, staining and other tests. The aspiration stylet only is promptly replaced to original position. The entire needle is given a twist in such a way that the marrow specimen inside the needle will break at the tip of the needle and remains inside the lumen. The needle with handle, the aspiration stylet in position, the biopsy specimen in its lumen are withdrawn. Next, the probe is introduced from the distal end of the needle towards the portal. In this process the solid marrow core biopsy is pushed and expressed out. The specimen is laid on a glass slide which is handed over to the Technnician for making "touch preparation" (smears) of marrow cells on the outer surface of marrow core. Then the biopsy is placed in formalin to be processed by the Pathologist. In summary, using single needle entering only once in the patient's marrow, two specimens, a solid core of marrow and liquid marrow are obtained for diagnosis. The patient is given a sterile dressing over the skin puncture site and ready to ambulate.

The biopsy portion of the needle can function as a conventional needle, in case only liquid marrow is desired, by applying suction with a syringe at the biopsy portal.

In summary, this invention overcomes the many inconveniences of existing bone marrow needles. First, this is a new method of obtaining both solid marrow core biopsy and liquid marrow sample in a single procedure. Second, the ergonomic design of the handle and cap help the operator to exert the necessary strong forces of pushing and twisting the needle to enter the hard bone. Third, the design of the needle with all parts fixed in the handle obviates any need for cumbersome assembly and dismantling of any parts. Fourth, the calibration of the outer portion of the needle gives the operator an estimation of the size of the marrow core which was blindly estimated by previous devices. Last but not the least, reducing the two procedures into one, the suffering by the patient both in duration and intensity of pain is reduced into half.

This device is most useful when both solid marrow core and liquid marrow sample are needed for best diagnostic yield of malignant diseases.

BRIEF DESCRIPTION OF THE DRAWINGS

FIG. 1: Is a prospective view of the bone marrow needle with the handle exposing the stylet heads in the portals meant for biopsy and aspiration of marrow according to a typical embodiment of the present invention.

FIG. 2: Is an overall view of the preferred embodiment when it is ready to be used by the operator with its cap on the head of the handle.

FIG. 3: Is an anatomical view of the needle and its portion inside the handle mould and focusing on the distal end of the needle.

FIG. 4: Is a circular blown up picture showing a detailed view of the distal end of the needle with the positions of the openings for lumina of the biopsy and aspiration portions of the needle with respective stylet tips in position.

FIG. 5: Is a cross section of the needle showing the shapes of the lumina for biopsy and aspiration portions of the needle with partition wall and stylets filling the respective lumina.

FIG. 6: Is a circular blown up picture of the distal end of the needle without the stylet tips showing the separate opening rims of lumina meant for biopsy and aspiration.

FIG. 7: Is a cross sectional view of the needle without the stylets in place, showing circular lumen meant for marrow core biopsy with a partition separating the semilunar lumen meant for liquid marrow aspiration.

FIG. 12: Is a postero superior view of the head of the handle of the device showing the positions of the stylet heads as seen by the operatior before the procedure for biopsy and aspiration of marrow.

FIG. 13: Is a postero superior view of the head of the handle without stylets, exposing the structures of the portals meant for biopsy and aspiration respectively.

FIG. 14: Is a postero superior view of the biopsy stylet as it appears when completely withdrawn by the operator.

FIG. 15: Is a postero superior view of the aspiration stylet as it appears when completely withdrawn by the operator.

FIG. 16: Is an overall view of the marrow probe with its spatula like handle and blunt distal tip.

DESCRIPTION OF THE PREFERRED EMBODIMENT

Figure 8:
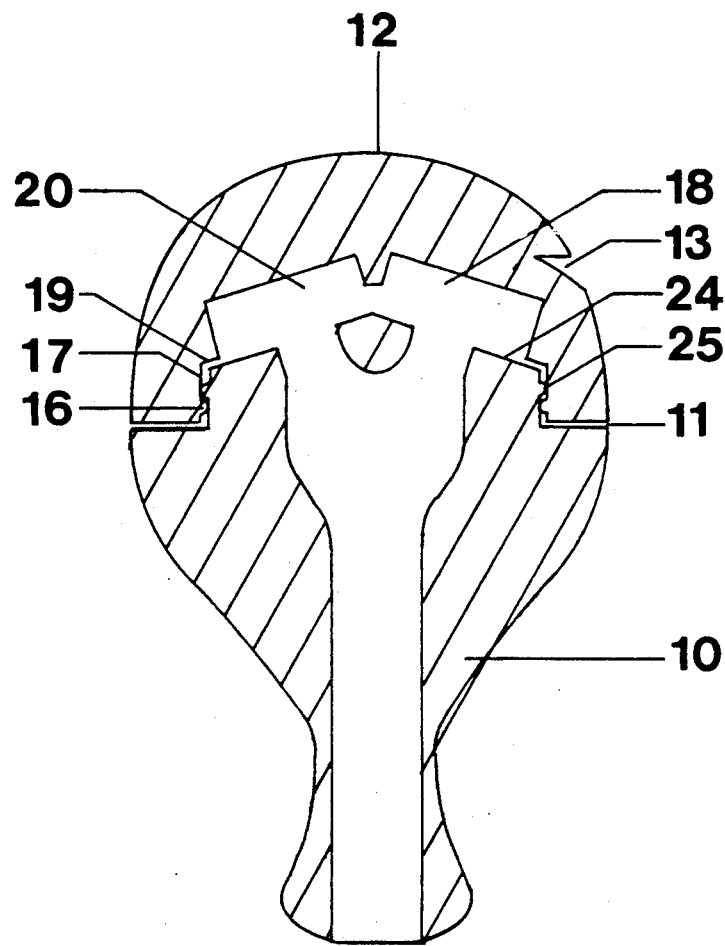
FIG. 8: Cross sectional view of the plastic handle mould with its body, head and fitting cap and spaces meant to fit the needle, portals and stylet heads.

For the purpose of promoting and understanding the principles of the invention, reference will now be made to the embodiment listed in the drawings and specific language will be used to describe the same. It will nevertheless be understood that no limitations of the scope of the invention thereby intended, such alterations and further modifications in the illustrated device, such further applications of the principles of the invention as illustrated there in being contemplated as would normally occur to one skilled in the art to which the invention relates.

Referring to the FIG. 1 & 2 there is illustrated a bone marrow needle 1, with its proximal portion encased in a plastic handle 10, for holding with fingers and thumb. Outwardly, the needle appears similar in size and shape and general configuration to bone marrow needles in use with eight to thirteen gauge bore and eight to ten centimeters in length. The needle of the invention is calibrated from outside with easily visible thin lines 2, half a centimeter apart.

The distal end of the needle has opening with cutting rim 3, for biopsy, through which protrudes the cutting edge 4, of the biopsy stylet. Close to the biopsy opening rim is another opening rim 5, meant for aspiration. Flush with this opening is the cutting edge 6, of aspiration stylet. Proximal to the opening rim 5, are a series of fenestrated openings 7, for further facilitation of liquid marrow entry.

The handle is ergonomically designed in a fusiform shape supplied with grooves 8, for index finger grip and grooves 9, for thumb grip. The partition between the head of the handle and the cap 12, is visible as a thin space 11, where both fit together. The cap is also shaped ergonomically in a dome shape. The outer surface of the cap is provided with uniquely designed grooves akin to finger prints of the hand to facilitate friction and grip over rubber gloves during operation. These grooves are not shown in the drawings lest we lose clarity. The cap is provided with a slot 13, for entry of thumb nail or other finger nail for lifting off the cap by the operator when needed. The cap is provided with a large lug 14, that fits snugly in a shelf like groove 32, in the body of the handle 10.

On opening the cap, the structures of the head of the handle 24, become visible as shown in FIG. 1. The head of the biopsy stylet 21, is shaped like a disk with vertical etchings on the rims for easy finger grip. The head is embossed clearly with a visible letter—"B" 22, indicating to the operator it is meant for marrow biopsy. ("B for biopsy" for easy memory). The head of the biopsy stylet is provided with a lug 23, to fit in snugly into the luer 27.

Next to the head of biopsy stylet is located similar head of the aspiration stylet 30. On the top of this head is clearly embossed a letter "A" 29, meant for aspiration ("A for aspiration" for easy memory). The head of the aspiration stylet is also provided with a lug 31, that fits in snugly in the luer 28.

The head of the handle 24, is ringed with a ridge 25, for "snap" fitting in a grove 16, inside the head fitting surface 17, of the cap. The resting surface 15, of the cap has identical surface corresponding to resting surface 26, of the body of the handle to receive the cap, to rest on the dome shaped head 24. The cap has a corresponding hollow dome shape 19, inside. This dome contains the capping surface 18, to cover the biopsy stylet head 21, and another capping surface 20, to cover the head 30, of the aspiration stylet. Thus, every structure an surface on the head of the handle is covered to exact proportions by the interior of the cap to prevent any movement of interior structures of the needle during operation for biopsy and aspiration. This cap obviates any need to assemble or dismantle any part unlike other devices in use.

Showing the handle mould as outline only in dotted lines in FIG. 3 illustrates the anatomy of the needle encased inside the handle. The needle 1, bifurcates proximally into two luers, one 27, to receive the biopsy stylet head 21, and the other 28, to receive aspiration stylet head 30. This arrangement gives the proximal portion of the needle a "double headed" appearance.

FIG. 3 focuses on the distal parts of the needle. Of note is the cutting surface 4, of the biopsy stylet is exactly in the same tangential plane of the cutting surface 6, of the aspiration stylet. This facilitates smooth entry of the needle into the hard bone as one cutting edge. The positions of the rim 3 of biopsy lumen, rim 5, of aspiration lumen and side openings 7, are illustrated clearly in the focusing circle. A detailed view of these structures is shown in the circular blown up FIG. 4.

FIGS. 5 and 7 are cross sectional views of the needle. The body of the biopsy stylet 33, is rounded to fit in the circular biopsy lumen 37. The body of the aspiration stylet 34, fits in the semilunar aspiration lumen 38. The lumens 37 and 38 are separated by partition wall 35, for the sake of clarity of illustration the total cross section of the needle appears slightly elliptical but in actuality the needle is circular.

FIG. 6 is the blown up details of the tip of the needle without stylets. Opening of the biopsy portion of the lumen 37, and opening 38 of the aspiration portion of the lumen are shown. It should be noted the biopsy lumen opening diameter is smaller than the diameter inside body of the needle due to gradual tapering portion 36.

The handle and the cap of the needle device can be entirely moulded from any cheap plastic like material. It could be opaque or a clear material making the encased portion of the needle visible as shown in FIG. 3. The entire mould is shown in cross section in FIG. 8. The dome shaped cap 12 shows a side slit 13, for thumb or finger nail to lift the cap off easily from the head when needed. The inner surface of the cap has capping surface 18, for the biopsy stylet head and capping surface 20, for aspiration stylet head. Rest of the inner dome surface 19, fits on the head of the handle 24. The capping grove 16, snap fits on ring of ridge 25 of the head. This grove and ridge mechanism is the easiest way for the operator to make the cap "snap" in or out. The resting surfaces of the cap and the body of handle are separated by a partition space 11.

Figure 10:
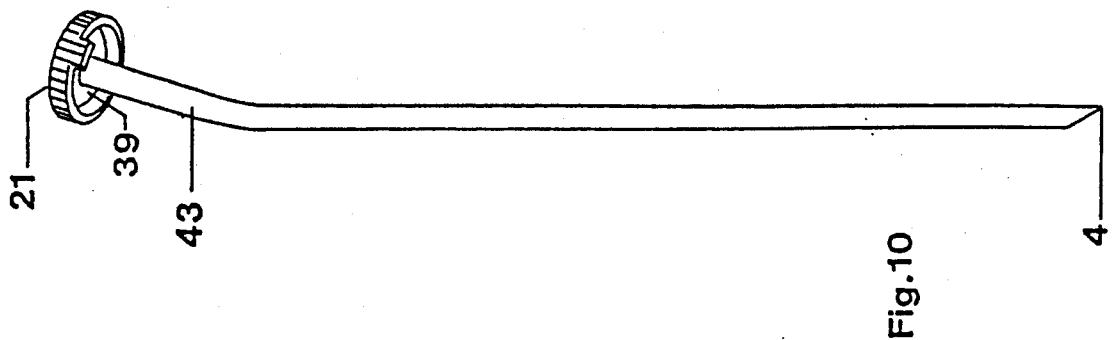
FIG. 10: Is a prospective view of the marrow biopsy stylet showing details of its head and proximal portion.
Figure 9:
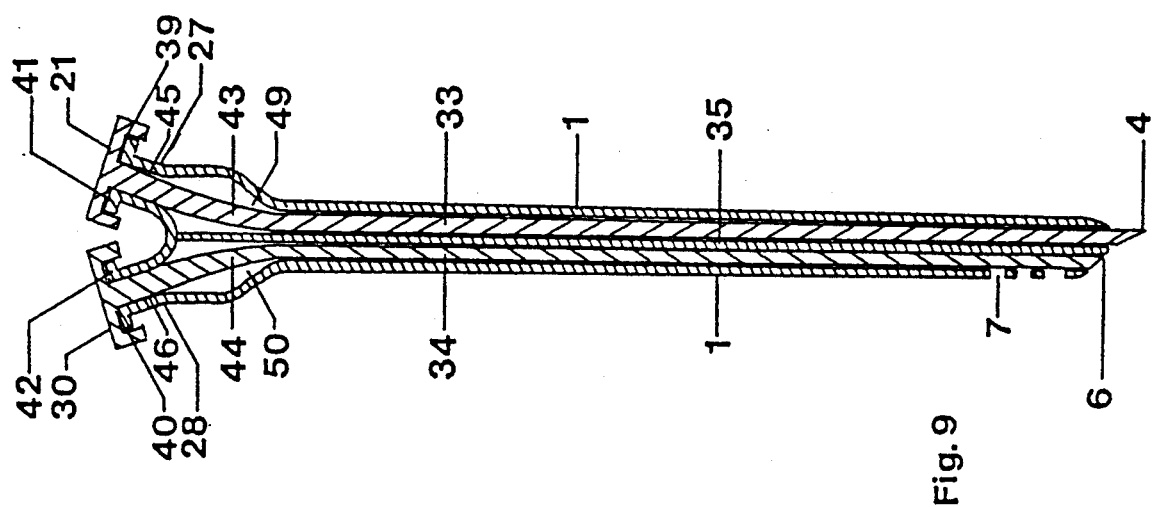
FIG. 9: Longitudinal sectional view of the entire mettalic needle assembly with stylets filling the lumina of the biopsy and aspiration portions of the needle and positions of openings at the distal end.
Figure 11:
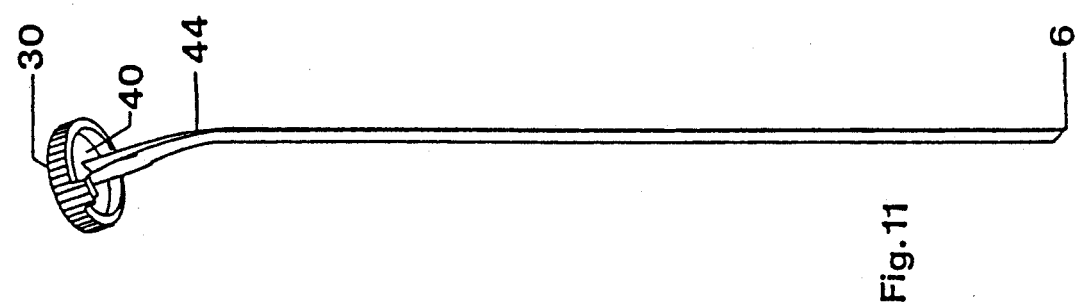
FIG. 11: Is a prospective view of the marrow aspiration stylet showing details of its head and proximal portion.

The unique design of this marrow device is that it is a two in one needle with two openings at the distal tip leading to two lumina of different cross sectional shapes and diameters, bifurcating proximally into two heads containing two portals. These features are best illustrated in the longitudinal cross section of the entire needle in FIG. 9 and the perspective views of the stylets, in FIGS. 10 and 11.

The disc shaped head of the biopsy stylet 21 has hollow inner surface 39, that rests on the luer edge 41, of the female luer 27. The proximal portion of the biopsy lumen takes a gentle curve 49, correspondingly the proximal portion of the biopsy stylet taking a very gentle curve 43. Finally, the biopsy lumen opens into the biopsy portal 45, for the entry of stylet or syringe. The distal end of the stylet with cutting surface 4, protrudes slightly beyond the rim of the opening of biopsy lumen.

The disc shaped head of the aspiration stylet 30, has a hollow inner surface 40, that rests on the luer edge 42, of the female luer 28.

The proximal portion of the aspiration lumen takes a gentle curve 50, corresponding to the gentle curve of the stylet 44. Finally, the aspiration lumen opens up into the aspiration portal 46. The distal end of the stylet ends flush with the tip of the aspiration lumen with its cutting surface 6.

FIG. 12 shows the operator's view of the handle with stylet heads when the cap is removed. This postero superior view shows biopsy stylet head 21, with letter "B" 22 indicating to the operator the location of biopsy portion and the corresponding lumen of the needle ("B" for biopsy). The aspiration stylet head 30, with letter "A" 29, clearly indicates to the operator the location of aspiration lumen inside the needle ("A" for aspiration).

FIGS. 13, 14 and 15 shows the operator's view of the needle handle with stylets removed. The portal 45, for the entry of the biopsy stylet is encircled by luer edge 41. Slot 47, in the luer edge is where the lug 23, of the biopsy stylet head snugly fits in the operating position shown in FIG. 12. Similarly, aspiration portal 46, is encircled by luer edge 42, containing slot 48, meant for lug 31, of aspiration stylet during procedure as shown in FIG. 12.

FIG. 16 shows the biopsy probe with elongated body 51, and a blunt tip 52. The proximal end is provided with spatula shaped flat handle 53. The handle is provided with ergonomically designed vertical groves for easy finger grip. The entire structure is made up of stainless steel.

Figure 17:
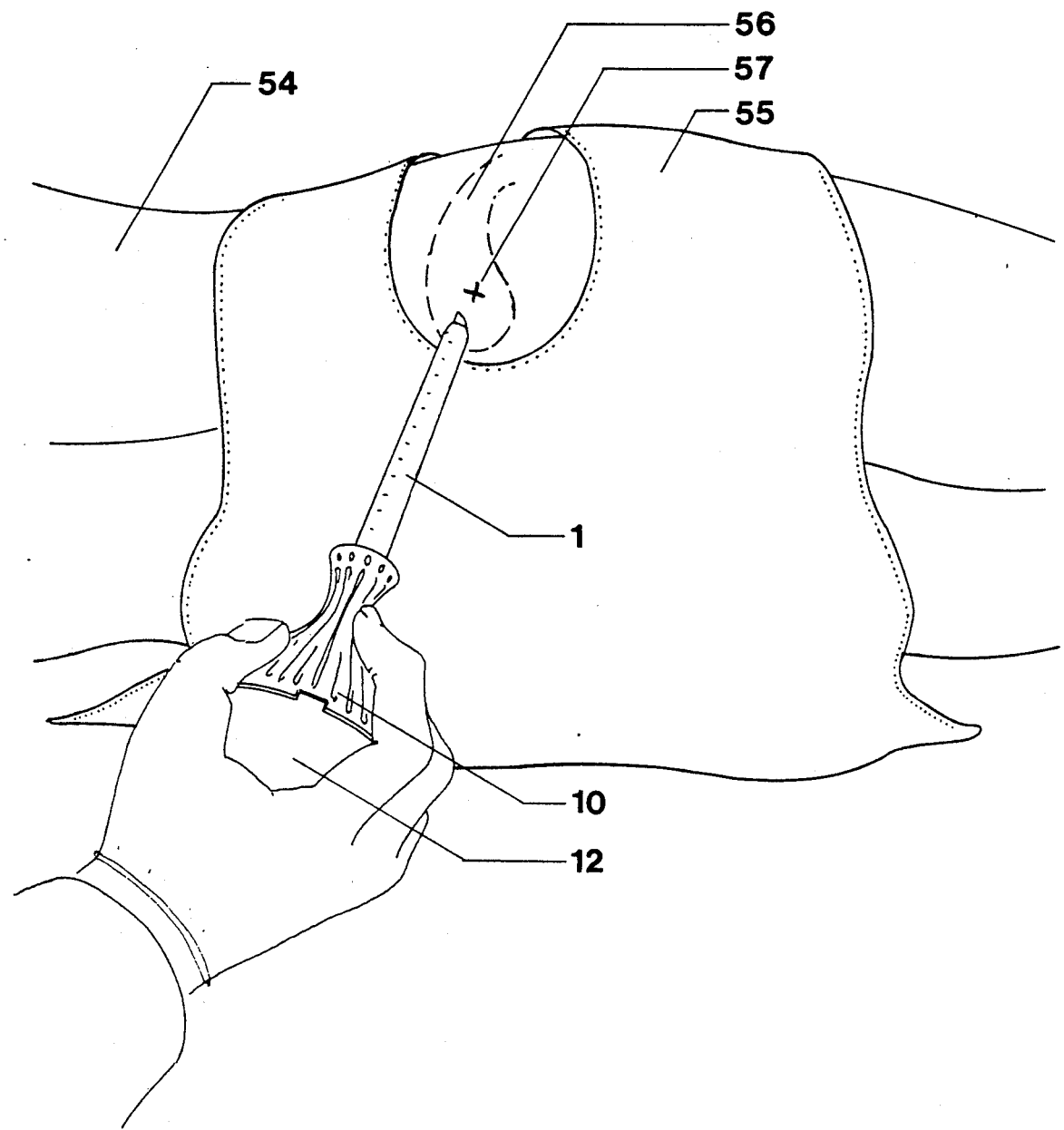
FIG. 17: A representative view of the patient's position for biopsy with the position of the right iliac crest marked for biopsy. The marrow needle is held comfortably by the operator in the right hand with the cap in the hollow portion of the hand. It shows the approach of the embodiment poised to enter the bone marrow.
Figure 18:
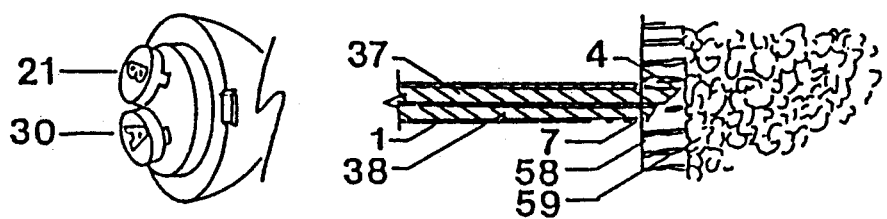
FIGS. 18-25: Shows the easy steps with which the needle is capable of obtaining both a solid core of marrow and a fluid sample by entering the marrow only once.
Figure 19:
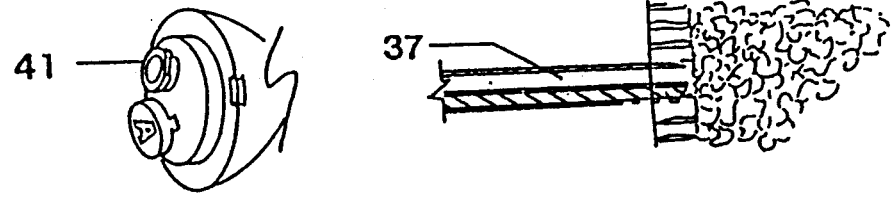
Figure 20:
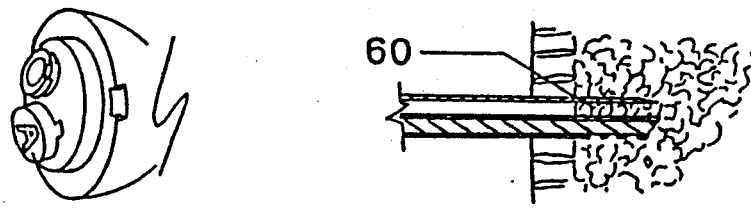
Figure 21:
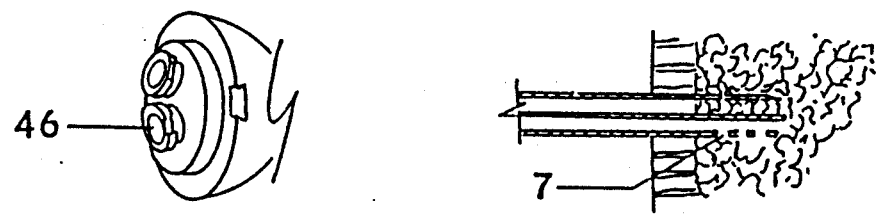
Figure 22:
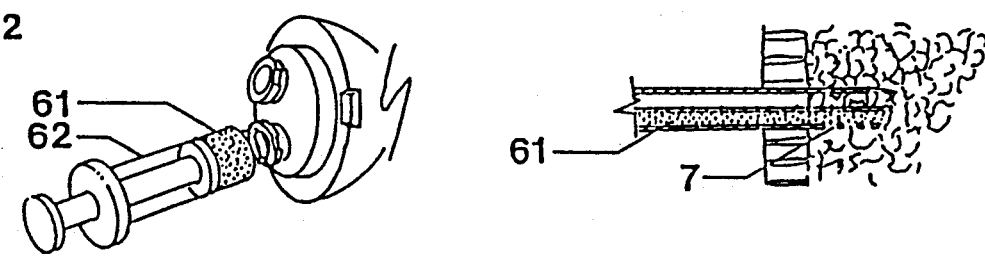
Figure 23:
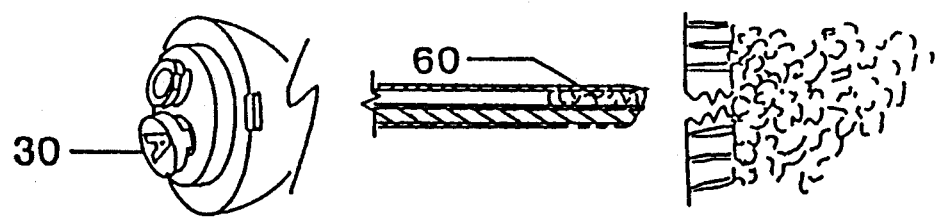
Figure 24:
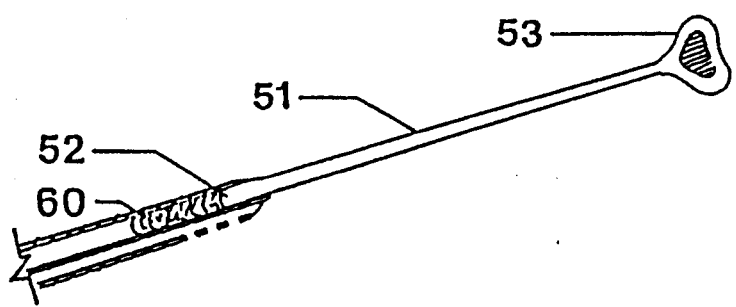
Figure 25:
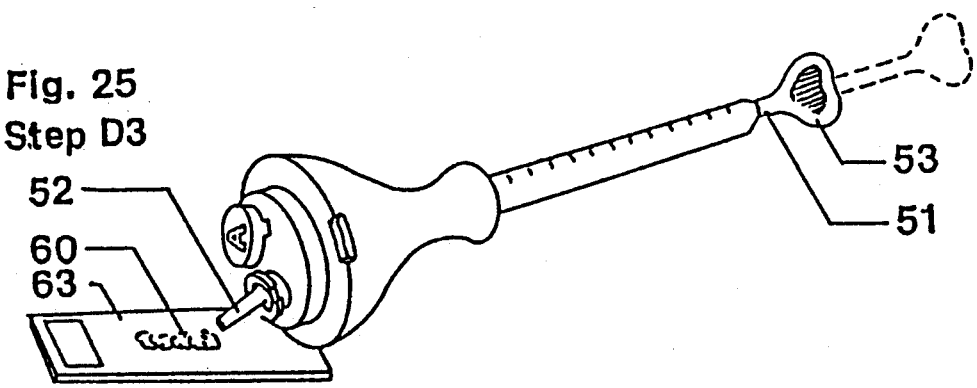

FIG. 17 shows the positioning of the patient for bone marrow aspiration and biopsy. The right hip 55, of the patient shows the outline of the right iliac crest 56. The location for entry of the needle is marked by X. The back 54, of the patient is facing the operator. The operator's hand is comfortably holding the needle poised to enter the iliac crest of the patient. The cap 12, of the handle snugly fits in the hollow of the operator's hand while the thumb and fingers firmly grip the body of the handle 10.

FIGS. 18-25 depict the easy steps by which both the speciments of marrow and aspirate are obtained.

Step A1

Shows the biopsy needle has just penetrated the cortex 58, of the iliac crest. The cap has been removed. The biopsy stylet head 21, and aspiration stylet are in their respective portals. Marrow 59, lies just underneath the cortex 58.

Step A2

The needle tip still in the cortex of the bone, biopsy stylet 21, is completely withdrawn. The aspiration stylet 30, is still in the position.

Step B

After replacing the cap the needle has been pushed into the marrow without the biopsy stylet. A core of marrow 60, has entered the hollow biopsy lumen.

Step C1

Aspiration stylet has also been removed. The tip of the aspiration lumen and side opening 7 have become patent in the marrow cavity.

Step C2

A syringe 62, is applied to the aspiration portal and a sample of liquid marrow 61, is aspirated.

Step D1

The aspiration stylet has been reintroduced into the aspiration lumen and the needle has been entirely withdrawn. The core of marrow biopsy 60, is still in the biopsy lumen.

Step D2

The tip 52, of the probe 51, as been introduced through the tip of the needle and the biopsy core 60, is being pushed out.

Step D3

The marrow biopsy specimen 60, is completely pushed out by the probe on a glass slide 63.

If the operator choses to obtain only liquid marrow aspirate but no biopsy, after entry of the needle a syringe can also be introduced in the biopsy portal to aspirate fluid marrow sample.

From the foregoing discussion it becomes clear that a bone marrow biopsy and aspiration needle device can be used on a patient with minimal discomfort to both the patient and the operator, avoiding the need to perform the procedure twice as needed with previous intruments. The unique design of the handle obviates any frustrating efforts of assembling or dismantling any parts. Considerable freedom is offered to the operator by the ergonomically designed contours of the handle. Any pain suffered by the patient is cut into half with integration of two procedures and due to the unique design of a needle, acquiring two distinct specimens of the solid core marrow biopsy and fluid aspirate with a single puncture of the bone.

It should be understood that although a marrow biopsy and aspiration needle has been illustrated with newly designed double lumen and heads with a ergonomically designed handle, the various features of disclosed invention are equally well suited to work every type of biopsy needle for bone or other soft tissued as well as any medical equipment that requires a needle and handle. Other various materials and connection techniques are possible. The optimal materials and dimensions will depend upon parts of the basic biopsy or aspiration needle style and other medical equipment as well as the intended application.

While the invention has been described in detail in the drawings and the foregoing description, the same is to be considered as illustrated and not restrictive in character. It being understood only the preferred embodiment has been shown and described and all changes and modifications that come within the spirit of the invention are desired to be protected.

What is claimed is:

1. A needle biopsy instrument, comprising:
    an elongate rigid hollow needle having proximal and distal ends, said needle having an aspiration lumen and a biopsy lumen extending along the length of said needle, said aspiration lumen and said biopsy lumen each having openings at said proximal and distal ends;
    a first stylet slidably received within said biopsy lumen and extending from said proximal end to said distal end of said needle; and
    a second stylet slidably received within said aspiration lumen and extending from said proximal end to said distal end of said needle;
    one of said first and second stylets having an end extending from the distal end of said needle and having a sharp cutting edge adapted to pierce a body bone for bone marrow biopsy such that when said stylet having a sharp cutting edge is withdrawn after piercing a body bone and said needle is further advanced a slice of marrow extends within said needle.

2. The needle biopsy instrument of claim 1 and further comprising:
    an instrument stabilizing means for stabilizing the position of said instrument as it is advanced inside a bone, said instrument stabilizing means further for facilitating the transmission of advancement forces along said instrument provided by the hand of an operator.

3. The needle biopsy instrument of claim 2 wherein said instrument stabilizing means includes a handle encasing the proximal end of said needle, said handle having a fusiform shape adapted to conform generally with the palm of the hand of an operator while being gripped between the thumb and fingers.

4. The needle biopsy instrument of claim 3 wherein said handle includes a head portion and a cap, said cap encasing the proximal end of said needle and removable from said head portion.

5. The needle biopsy instrument of claim 1 wherein said first stylet having a sharp cutting edge extending from the distal end of said needle adapted to pierce a body bone for bone marrow biopsy.

6. The needle biopsy instrument of claim 1 wherein said needle and said first and second stylets each having locking means for locking the position of said first and second stylets within their respective lumens at the proximal end of said needle.

7. The needle biopsy instrument of claim 6 wherein said locking means associated with said first and second stylets each have a head portion having a generally disk shape.

8. The needle biopsy instrument of claim 1 wherein said biopsy lumen having a circular cross section along its length and said aspiration lumen having a semilunar cross section along its length, said needle having a thin wall separating said biopsy lumen and said aspiration lumen.

9. The needle biopsy instrument of claim 1 wherein said aspiration lumen having a plurality of fenestrated openings extending laterally of said needle.

10. The needle biopsy instrument of claim 1 wherein said second stylet having a distal tip formed to extend flush with the distal opening of said aspiration lumen and parallel to the cutting surface of said first stylet.

11. The needle biopsy instrument of claim 1 wherein said stylets each having heads at the proximal ends thereof adapted to extend from the body portion of said handle with said stylets locked in position inside their respective needle lumens.

12. The needle biopsy instrument of claim 1 wherein said cap is provided with an inner surface which conforms closely around said stylet heads with said stylets in their locked positions relative to said needle.

13. The needle biopsy instrument of claim 1 and further comprising an elongate probe sized to be slidably advanced within said biopsy lumen through said opening at said distal end, said elongate probe having a blunt tip and having a proximal end formed as a spatula shaped handle.

14. The needle biopsy instrument of claim 1 wherein said needle is marked with a plurality of graduated markings along its length.

* * * * *